United States Patent [19]

Webber

[11] Patent Number: 5,268,504
[45] Date of Patent: Dec. 7, 1993

[54] PROCESS FOR THE CONVERSION OF SULFATES TO SULFONATES

[75] Inventor: Kenneth M. Webber, Houston, Tex.

[73] Assignee: Exxon Production Research Company, Houston, Tex.

[21] Appl. No.: 920,932

[22] Filed: Jul. 28, 1992

[51] Int. Cl.$^5$ .......................................... C07C 309/10
[52] U.S. Cl. ..................................... 562/120; 562/42; 562/110
[58] Field of Search .......................... 562/120, 110, 42

[56] References Cited

U.S. PATENT DOCUMENTS

| | | | |
|---|---|---|---|
| 4,223,164 | 9/1980 | Yang et al. | 568/618 |
| 4,283,321 | 8/1981 | Chakrabarti et al. | 562/42 |
| 4,453,023 | 6/1984 | McCain et al. | 568/618 |
| 4,792,419 | 12/1988 | Piorr et al. | 562/110 |
| 4,959,490 | 9/1990 | Parnell et al. | 562/74 |
| 4,978,780 | 12/1990 | Fikentscher et al. | 562/110 |

FOREIGN PATENT DOCUMENTS

| | | | |
|---|---|---|---|
| 0344835 | 5/1989 | European Pat. Off. | 43/11 |
| 0361620 | 9/1989 | European Pat. Off. | 43/11 |
| 0398450 | 5/1990 | European Pat. Off. | 43/11 |

OTHER PUBLICATIONS

"Alkylethoxyethanesulphonates: Two Techniques for Improving Synthetic Conversions"; P. K. G. Hodgson, N. J. Stewart, C. E. Grand & A. M. Nicholls; The British Petroleum Company pic, Research Centre, New Technology Div., JAOCS, vol. 67, No. 11 (Nov. 1990).

Primary Examiner—Marianne M. Cintins
Assistant Examiner—John Peabody
Attorney, Agent, or Firm—Susan A. McLean

[57] ABSTRACT

Disclosed is a process for increasing the selectivity in converting sulfates to sulfonates following ethoxylation and sulfation of alcohols. It is demonstrated that minimization of unethoxylated and monoethoxylated alcohols before the sulfation step will substantially reduce hydration to alcohols and increase the selectivity of the subsequent sulfonation step.

2 Claims, 1 Drawing Sheet

PROCESS FOR THE CONVERSION OF SULFATES TO SULFONATES

BACKGROUND OF THE INVENTION

1. Field of the Invention

This invention relates to an improved process for the manufacture of alkylethoxy ethane sulfonates, an important class of surfactants. Specifically, a method of improving the selectivity of the sulfate-to-sulfonate reaction is disclosed.

2. Description of the Related Art

Sulfonate surfactants are well known for their stability at elevated temperatures. Unlike sulfate surfactants, these sulfonate compounds can withstand the rigors of a high-temperature, low-pH environment for extended lengths of times. Two common forms of sulfonates are alkyl aryl sulfonates (1) and alkenyl sulfonates (2):

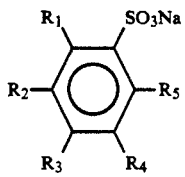

$R_6CH=CHCH_2SO_3Na$ (2)

An emerging technology that may require significant quantities of sulfonates is Enhanced Oil Recovery (EOR). It has been demonstrated that by adding surfactant to the water flood process of oil recovery, one can increase significantly the amount of oil recovered from a particular reservoir. For the surfactant to be effective at producing more oil, it must stay in solution within the brine phase used for the water flood. Many of the brines reinjected into the reservoir contain relatively high concentrations of divalent cations such as calcium or magnesium. Unfortunately, both alkyl aryl sulfonates and alkenyl sulfonates are sensitive to divalent cations and tend to precipitate from solution in their presence.

It is well known that this sensitivity to divalent cations can be overcome by incorporating a number of ethyl ether linkages into the molecule. The most common type of this surfactant is alkylethoxy ethane sulfates. As sulfates, the compounds do not have sufficient thermal stability to be used in all reservoirs. A less common class of surfactant, alkyl ethoxy ethane sulfonates, has both the divalent cation tolerance and the high temperature, low pH stability necessary to make it viable for nearly all reservoir conditions. One major drawback of their use is that alkylethoxy ethane sulfonates are relatively expensive surfactants to manufacture.

One common method of producing these compounds is to produce the corresponding sulfate from alcohols or phenols, then convert it to the sulfonate by reaction with sodium sulfite. This is thus a three step process:

(1) $R\text{---}OH + nC_2H_4O \rightarrow R(EO)_nOH$ where
- $R$ = an alkyl or phenyl group
- $n$ = an integer, generally between 0 and about 10
- $EO$ = ethylene oxide $(C_2H_4O)$ (2) $HSO_3Cl + R(EO)_nOH \rightarrow R(EO)_nOSO_3H$ (3) $R(EO)OSO_3H + Na_2O_3S \rightarrow R(EO)_nOSO_2Na$ A major factor in the cost of producing sulfonates by this route is the low selectivity of the conversion of the sulfate to the sulfonate (step 3). Any improvement in the selectivity of this step would result in a lower cost sulfonate. In the process, the sulfating agent alternatively may be $SO_5$.

SUMMARY OF THE INVENTION

It is well known that, during the first step of the process above described (the ethoxylation step), a diverse distribution of products is formed. That is, there will be products with no ethylene oxide group adducted to the alcohol, some with one group adducted, some with two, and some with more. It has been found that, upon modification of this distribution such that there is a significantly lower concentration of species with zero ethoxy groups ("$EOe_0$") or one ethoxy group ("$EO_1$") in the ethoxyalcohol mix, the selectivity of the sulfates made from this modified oxyalcohol in the subsequent reaction to produce the sulfonate may be increased.

Two alternative methods are suggested for producing an ethoxyalcohol mixture with relatively few $EO_0$ and $EO_1$ molecules. The first method requires a distillation step after formation of the ethoxyalcohol but before the sulfation step (that is, between steps 1 and 2). This distillation will remove the lighter boiling components, which should include most of the $EO_0$ and $EO_1$ species.

The second method uses a narrow-range ethoxylation catalyst, such as the calcium based catalysts of U.S. Pat. No. 4,835,321 to Leach et al; the promoted barium catalysts of U.S. Pat. No. 4,456,023 to McCain et al; the strontium base catalysts of U.S. Pat. No. 4,223,164 to Young et al; the lanthanum silicates and metasilicates of U.S. Pat. No. 4,960,952 to Kemp; the barium oxide of U.S. Pat. No. 4,239,917 to Young; the metal-containing bimetallic or polymetallic catalyst of European Patent Application Publication No. 0361620A2 by Union Carbide Chemicals and Plastics Company, Inc.; the barium phosphate catalysts of European Patent Application Publication No. 039845 by Shell Internationale Research Maatschapping B.V.; or any other such narrow range ethoxylation catalysts as may presently be known or may become known in the art; during the ethoxylation step (step 1). The use of such catalysts will result in an ethoxyalcohol mix with far fewer $EO_0$ and $EO_1$ components than result from the uncatalyzed reaction.

DETAILED DESCRIPTION OF THE INVENTION

Figure 1:
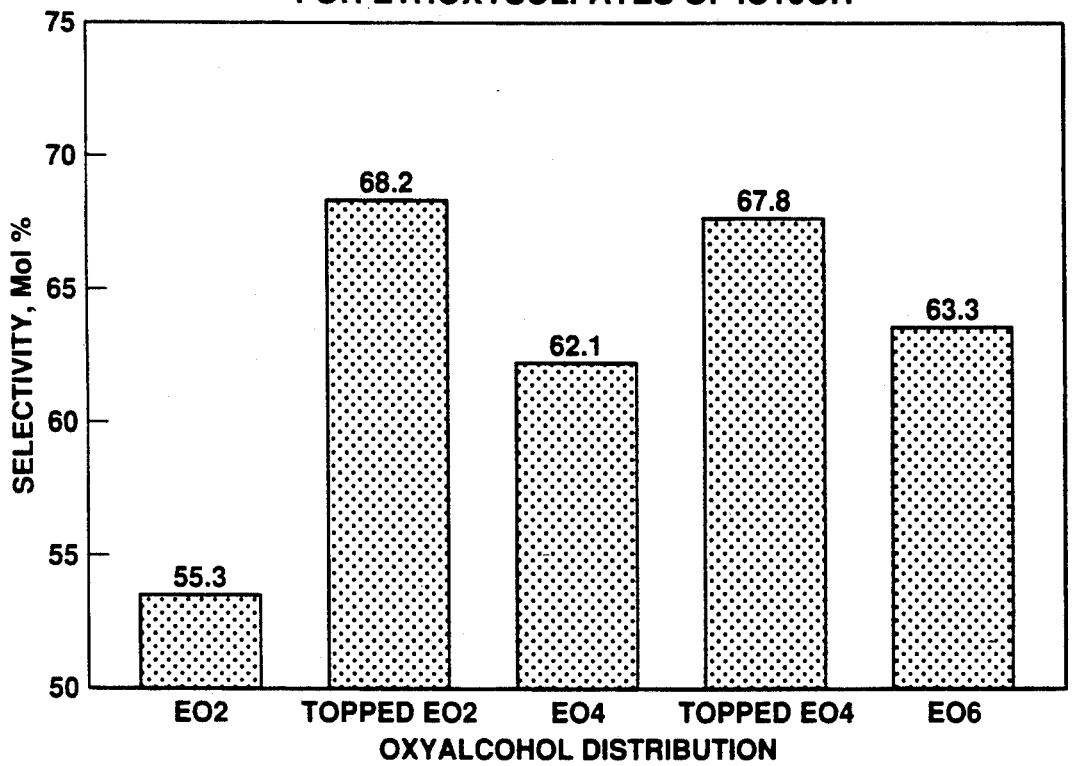
FIG. 1 is a graphical depiction of the selectivity attained for various versions of topped and untopped ethoxyalcohols, as discussed in the Example herein.

There are two primary ways to modify the ethylene oxide distribution. One is simply to distill the normal product to remove the lighter boiling compounds - - - those with low numbers (0 or 1) of EO adducts. The second method is to choose the catalyst system for the ethoxylation to produce a distribution with lower concentrations of these undesirable structures.

As one can see from FIG. 1, as the average length of the ethoxylate chain increases from two to four to six, the molar selectivity increases. One might think that the increase in selectivity resulting from the removal of the non-ethoxylated structures or the mono-ethoxylated structures might simply be due to the resultant increase in the average ethoxy chain length. This is not the case. The distillation of the structure with an average of two ethoxy units per alcohol resulted in about 33% of the material being removed. If all the material were non-ethoxylated alcohol, the resultant structure would have an average of 3.5 moles of ethylene oxide adducted per alcohol moiety. The selectivity for this structure is greater than either that with a normally distributed four moles or six moles of ethylene oxide adducted to the alcholol. Clearly the distillation has more effect than to just increase the average length of the ethoxy chain.

EXAMPLE

A sample of a branchy $C_{16}$ alcohol was ethoxylated three different times, once to generate a product with an average of 2 moles EO per mole alcohol, once to produce an average $EO_4$ structure and once to produce the average $EO_6$ structure. A portion of the $EO_2$ structure and of the $EO_4$ structure were each topped by distillation to remove any unethoxylated $C_{16}$ alcohol. Each of these five oxyalcohols were sulfated and the sulfates in turn were reacted with sodium sulfite to produce alkylethoxy ethane sulfonates. The products from the five displacement reactions were all carefully analyzed to determine the number of moles of sulfonate produced per mole of sulfate reacted (called selectivity). The results from that analysis are presented in FIG. 1. It can be seen that removing the unethoxylated alcohol has substantially improved the molar selectivity of the reaction. Topping the $(EO)_2$ structure improved the selectivity from 55.3 mol% to 68.2 mol% and topping the $(EO)_4$ structure improved the selectivity from 62.1 mol% to 67.8 mol%.

What is claimed is:

1. A process for the synthesis of alkylethoxy ethane sulfonates, comprising:
    a) ethoxylation of a branchy $C_{16}$ alcohol to produce an ethoxyalcohol.
    b) elimination of unreacted alcohols, as well as those alcohol molecules with only one ethoxy group; wherein said elimination is performed by distillation;
    c) reaction of the remaining ethoxyalcohols with a sulfating agent to form an alkylethoxy ethane sulfate; and
    d) reaction of the alkylethoxy ethane sulfate with sodium sulfite to produce alklethoxy ethane sulfonate.

2. The process of claim 1 wherein the sulfating agent is $SO_3$ or $HSO_3Cl$.

* * * * *